(12) United States Patent
Khan et al.

(10) Patent No.: US 8,178,012 B1
(45) Date of Patent: May 15, 2012

(54) SHADED ZIRCONIUM OXIDE ARTICLES AND METHODS

(75) Inventors: Ajmal Khan, Princeton, NJ (US); Carlino Panzera, Hillsborough, NJ (US); Dmitri G. Brodkin, Livingston, NJ (US)

(73) Assignee: Ivoclar Vivadent AG, Schaan (LI)

( * ) Notice: Subject to any disclaimer, the term of this patent is extended or adjusted under 35 U.S.C. 154(b) by 1212 days.

(21) Appl. No.: 11/717,199

(22) Filed: Mar. 13, 2007

Related U.S. Application Data

(60) Provisional application No. 60/789,610, filed on Apr. 6, 2006.

(51) Int. Cl.
A61C 13/00 (2006.01)
A61C 13/083 (2006.01)

(52) U.S. Cl. .......................... 264/20; 264/16

(58) Field of Classification Search .......... 264/20
See application file for complete search history.

(56) References Cited

U.S. PATENT DOCUMENTS

| | | |
|---|---|---|
| 3,984,524 A | 10/1976 | Alexandrov et al. |
| 4,742,030 A | 5/1988 | Masaki et al. |
| 5,011,403 A | 4/1991 | Sadoun et al. |
| 5,043,316 A | 8/1991 | Janssens et al. |
| 5,219,805 A | 6/1993 | Yoshida et al. |
| 5,656,564 A | 8/1997 | Nakayama et al. |
| 5,698,482 A * | 12/1997 | Frank et al. ............. 501/10 |
| 6,030,209 A | 2/2000 | Panzera et al. |
| 6,380,113 B1 | 4/2002 | Kim et al. |
| 6,709,694 B1 | 3/2004 | Suttor et al. |
| 6,713,421 B1 | 3/2004 | Hauptmann et al. |
| 7,011,522 B2 | 3/2006 | Panzera et al. |
| 2004/0156986 A1 * | 8/2004 | Yadav .................... 427/180 |
| 2005/0023710 A1 | 2/2005 | Brodkin et al. |

FOREIGN PATENT DOCUMENTS

| | | |
|---|---|---|
| FR | 2 781 366 | 7/1998 |
| JP | 2-145475 | 6/1990 |
| JP | 3-28161 | 2/1991 |
| JP | 5-43316 | 2/1993 |
| JP | 2005-289721 | 10/2005 |
| WO | WO 2004021921 A1 * | 3/2004 |

OTHER PUBLICATIONS

B. Cales, "Colored Zirconia Ceramic for Dental Applications," Bioceramics vol. 11, edited by R. Z. LeGeros and J. R. LeGeros; Proceedings of the 11th International Symposium on Ceramics in Medicine; York, NY; Nov. 1998.

P. Duran et al., "Preparation, Sintering, and Properties of Translucent $Er_2O_3$-Doped Tetragonal Zirconia," J. Am. Ceram. Soc., vol. 72, No. 11, pp. 2088-2093, 1989.

M. Yashima et al., "Effect of Dopant Species on Tetragonal (t')-to-Monoclinic Phase Transformation of Arc-Melted $ZrO_2$-$RO_{1.5}$ (R = Sm, Y, Er, and Sc) in Water at 200° C and 100 MPa Pressure," J. Am. Ceram. Soc., No. 78, No. 8, pp. 2229-2293, 1995.

(Continued)

*Primary Examiner* — Yogendra Gupta
*Assistant Examiner* — Alison Hindenlang
(74) *Attorney, Agent, or Firm* — Ann M. Knab; Thad McMurray

(57) ABSTRACT

A dental article includes yttria stabilized tetragonal zirconia polycrystalline ceramic, and no more than about 0.15 wt. % of one or more coloring agents of one or more of: Pr, Tb, Cr, Nd, Co, oxides thereof, and combinations thereof, whereby the dental article is provided with a color corresponding to a natural tooth shade; and wherein the dental article has a flexural strength of at least about 800 MPa. Corresponding methods are also described.

31 Claims, 1 Drawing Sheet

OTHER PUBLICATIONS

K. C. Shah et al., "Physical Properties of Cerium-Doped Tetragonal Zirconia," Abstract 0800, Journal of Dental Research, vol. 85, Special Issue A, 2006.

International Standard—ISO 6872, "Dental Ceramic", 1995 (E).

Zirconia Powder Series "B" Grades; http://www.tosoh.com/Products/b+basic_grades.htm ; Tosoh Corporation: The Chemistry of Innnovation; p. 1 of 1.

* cited by examiner

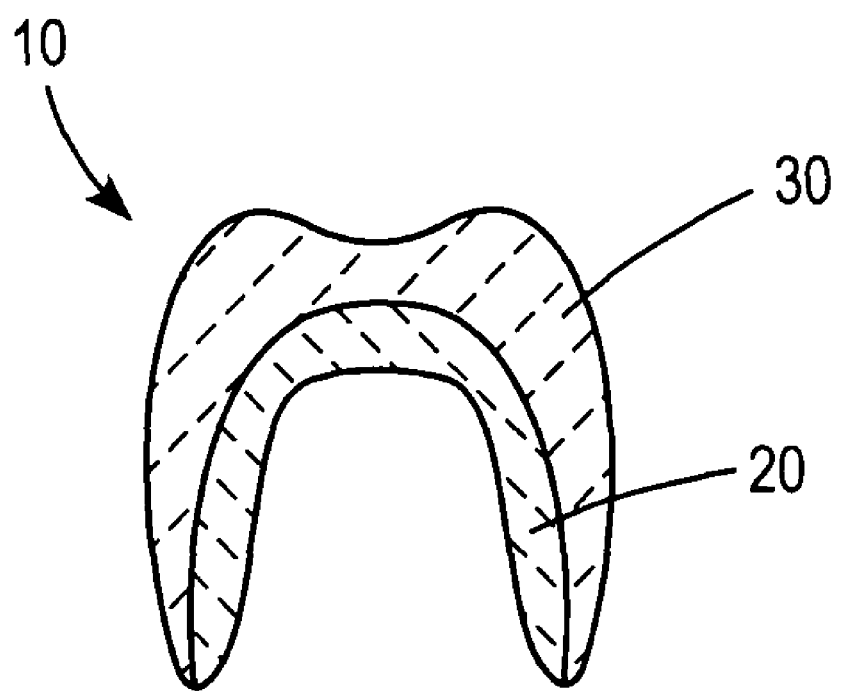

SHADED ZIRCONIUM OXIDE ARTICLES AND METHODS

The present application claims priority under 35 U.S.C. §119 to U.S. Patent Application Ser. No. 60/789,610 filed Apr. 6, 2006, the entire content of which is incorporated by reference herein.

BACKGROUND

In the discussion of the state of the art that follows, reference is made to certain structures and/or methods. However, the following references should not be construed as an admission that these structures and/or methods constitute prior art. Applicant expressly reserves the right to demonstrate that such structures and/or methods do not qualify as prior art.

Yttria Tetragonal Zirconia Polycrystalline (YTZP) materials have emerged as a high-strength framework material for dental prostheses (single-units up to multiple unit bridges). However due to its inherent white color, often the esthetics of the finished restoration is inferior to what is achievable with other all-ceramic systems.

Currently there are two predominant commercially available methods to deal with the stark white color of zirconia. In the one method, the color of the zirconia is "hidden" by applying either a layer of stain or liner. The other method entails shading the zirconia by immersion in, or painting with, coloring solutions while in the pre-sintered state. Coloring with a stain and/or applying a liner involves an extra fabrication step and lowers translucency. Shading with a coloring solution similarly requires the extra step of dipping or painting, and extra time to dry before sintering. Also, this method is deficient as the color of the final sintered framework often is not uniform.

An alternative method is to use porous zirconia blocks that are preshaded to the desired coloration. Such blocks only need to be fired after any machining, thus eliminating the coloring with solutions step. As the fully sintered frameworks emerge from the furnace already shaded, the stain/liner step can be eliminated. Additionally, the color of the sintered frameworks is characteristically uniform, which is another advantage over the shading with coloring solution method.

A finished dental restoration should match the color of the patient's teeth, i.e., it should be "tooth colored". The colors of human teeth appear to range from a light almost white-tan to a light brown, and occupy a very specific color space. This color space can be described by the commonly used CIE (Commission Internationale de l'Eclariage) L*, a*, b* conventions, which represents colors in a three-dimensional Cartesian coordinate system. L*, or "value", is a measure of luminance or lightness, and is represented on the vertical axis. The a*, b* coordinates, are a measure of chromaticity and are represented on the horizontal coordinates, with positive a* representing red and negative a* representing green, and positive b* representing yellow and negative b* representing blue. U.S. Pat. No. 6,030,209, which is incorporated herein by reference, presents the CIE L*, a*, b* color coordinates of tooth colors represented by the Vita Lumen® shade guide system manufactured by Vita Zahnfabrik (i.e., it presents the color space of tooth colors). Herein, "tooth color" is taken to mean CIE L*, a*, b* color coordinates that fall within, or very close to, this color space.

U.S. Pat. No. 6,713,421 appears to describe yttria-stabilized zirconia dental milling blanks that are formed with 0-1.9 wt. % coloring additives. The composition described therein includes 0.1 to 0.50 wt. % of at least one oxide of aluminum, gallium, germanium and indium for the purpose of lowering the sintering temperature and increasing stability and hydrolytic resistance in the densely sintered state. However, the addition of aluminum oxide (alumina) to zirconia also often results in discrete alumina inclusions distributed throughout the microstructure. This occurs in part due to the low solubility of alumina in zirconia. Further, it presents a particular disadvantage for dental applications because alumina inclusions can lower the translucency of the zirconia since the refractive index of alumina, 1.77, differs considerably from that of tetragonal zirconia, 2.16. Thus, it is desirable that dental zirconia is devoid of any alumina inclusions. A means to achieve this is to minimize, or eliminate, the alumina addition, thereby minimizing the potential for the alumina inclusions in the final microstructure.

In U.S. Pat. No. 6,713,421 the blanks are made from powders or granules that have been doped with the various oxides via a solution followed by a co-precipitation method. The cited advantage of this method is that the various oxides are distributed homogeneously throughout the powder. However, the field of dental restoratives requires many shades (e.g., 7 zirconia core shades as per LAVA, 16 Vita Classic shades, etc.), and having to prepare so many individually shaded powders or granules can be cost-prohibitive.

Yet another disadvantage of U.S. Pat. No. 6,713,421 is that it requires relatively large amounts of the preferred coloring oxides, iron oxide and erbium oxide. This is revealed by the Preparation Example 1 cited which teaches adding 0.2 wt. % iron oxide+0.38 erbium oxide (0.58% total) to color 3YTZP. Although the patent does not indicate if this resulted in a tooth color, it can be inferred from U.S. Pat. No. 5,219,805, which appears to disclose coloration of yttria-stabilized zirconia for dental bracket applications using combinations of $Fe_2O_3$, $Er_2O_3$, and $Pr_6O_{11}$, that even higher $Fe_2O_3$ and $Er_2O_3$ concentrations are necessary to achieve tooth coloration. For instance, according to the examples given in U.S. Pat. No. 5,219,805, up to 1.0 mol % $Er_2O_3$ (3.0 wt. %) additive is required to achieve dental brackets "having color tone similar to ivory-colored teeth". Additionally, up to 0.2 mol % $Fe_2O_3$ (0.25 wt. %) is required to achieve tooth colors, which although less than the 1 mol % $Er_2O_3$ required, is a considerable amount. As such quantities are significant, they can have a negative effect on other properties of the resulting YTZP cores, such as on strength, weibull modulus, hydrolytic resistance, and grain size.

Additionally, it has been observed that $Er_2O_3$ additions to 3Y-zirconia, of 0.2 wt. % or greater, results in sintered bodies that fluoresce a dark yellow under ultraviolet (UV) lighting. This is inappropriate for a dental framework, which under UV, ideally, should fluoresce bluish-white to mimic that of natural teeth. Less ideally, the framework should not fluoresce at all in the visible light range. In the latter case fluorescence is typically imparted to the final restoration by the overlay porcelains. The shortcoming of an inappropriate fluorescence is overcome by the present invention.

The prior art also shows Cr additions result in green or brown coloration. For example, U.S. Pat. No. 3,984,524 appears to describe olive coloration of cubic zirconia with addition of 0.1 to 2 wt. % $Cr_2O_3$, U.S. Pat. No. 4,742,030 appears to describe green coloration of 5 mol % yttria-stabilized zirconia with addition of 0.7 wt. % $Cr_2O_3$, and brown coloration with addition of 0.2 wt. % $Cr_2O_3$, respectively.

French patent publication 2,781,366 and Cales et. al. ("Colored Zirconia Ceramics for Dental Applications," Bioceramics Vol. 11, edited by R. Z. LeGeros and J. R. LeGeros; Proceedings of the 11th International Symposium on Ceramics in Medicine; York, N.Y.; November 1998) appear to identify a number of colorants, and was reportedly successful in achieving some of the Vita shades in 3YTZP by using combinations of $Fe_2O_3$, $CeO_2$ and $Bi_2O_3$. However, their choice of colorant oxides is a drawback as they are required in fairly large amounts to achieve some of the desired shades.

U.S. Pat. No. 5,656,564 appears to teach coloration of zirconia for dental bracket applications using with combinations of $Er_2O_3$ and $Pr_6O_{11}$. The sintered zirconia-based ceramic is produced by a procedure generally including combining constituents in solution, precipitating, calcining, pressing, and sintering.

U.S. Pat. No. 5,011,403 appears to describe coloration of zirconia dental brackets using combinations of one or more of oxides of Fe, Ni and Mn added to a Zr-based powder.

U.S. Pat. No. 6,709,694 appears to describe the use of solutions for coloring of pre-sintered zirconia dental frameworks by immersion, painting or spraying using a metal ion coloring solution or metal complex coloring solution that is applied to a presintered ceramic, followed by sintering to form a translucent, colored dental ceramic. The claimed ions or complexes are of the rare earths elements or subgroups II and VIII, with an action time of under two hours, and maximum pre-sintered zirconia diameter and height of 10 and 7 mm, respectively. However, this method is not ideal as the color of the final sintered frameworks often are not uniform and the process requires the extra steps of applying the solutions and drying prior to sintering.

The development of pink coloration in zirconia by Er additions is described in (i) P. Duran, P. Recio, J. R. Jurado, C. Pascual and C. Moure, "Preparation, Sintering, and Properties of Translucent $Er_2O_3$-Doped Tetragonal Zirconia," J. Am. Ceram. Soc., vol. 72, no. 11, pp. 2088-93, 1989; and (ii) M. Yashima, T. Nagotome, T. Noma, N. Ishizawa, Y. Suzuki and M. Yoshimura, "Effect of Dopant Species on Tetragonal (t')-to-Monoclinic Phase Transformation of Arc-Melted $ZrO_2$—$RO_{1.5}$ (R=Sm, Y, Er, and Sc) in Water at 200° C. and 100 MPa Pressure," J. Am. Ceram. Soc., no. 78, no. 8, pp. 2229-93, 1989. Additions of CoO, $Fe_2O_3$ and $Cr_2O_3$ combinations to yttria-stabilized zirconia are known to impart a blue color in the final sintered zirconia bodies, as apparently described in Japanese patent publication 2,145,475. Additions of one or both of the colorants, Ni oxide and Cobalt oxide, to yttria-stabilized zirconia have been shown to result in a purplish colored sintered body, as apparently described in U.S. Pat. No. 5,043,316.

Japanese patent publication 3,028,161 appears to describe the preparation of colored zirconia by the steps of: (1) mixing zircon-based pigment with partially stabilized zirconia containing $Y_2O_3$, MgO, etc., (2) molding and (3) sintering to provide a colored zirconia sintered product.

Many of the aforementioned coloring additions can negatively affect not only mechanical properties, including strength and fracture toughness, but also isotropic shrinkage and final sintered density. This can happen for a number of reasons including: (1) loss of fracture toughness from a lowering of the "transformation toughening" effect as a result of the over-stabilization of the tetragonal phase by the additive (either chemically, or by grain size reduction) thereby hindering the transformation from the metastable tetragonal phase to monoclinic phase that is necessary for the toughening to happen, (2) loss of strength due to spontaneous microcrack formation that can result if grains grow too large because of the additive, and, (3) loss of strength due to the formation of strength-limiting pores in the microstructure due to the additive. This last reason is what Shah et al. (K. C. Shah, I. Denry and J. A. Holloway, "Physical Properties of Cerium-Doped Tetragonal Zirconia," Abstract 0080, Journal of Dental Research, Vol. 85, Special Issue A, 2006) attribute the significant loss of strength, down to 275±67 MPa, for 3YTZP materials that were colored using Ce salts. Additionally, they observed that strength decreased linearly with the concentration of the coloring additive, Ce.

The problem of formation of coarse pores, along with grain growth, in colored zirconia sintered compacts has also been recently recognized in JP 2005289721.

It is also important to recognize that only certain combinations of coloring agents in certain proportions will enable the matching of the color of a dental article so as to match the desired natural tooth color, e.g., A, B, C, D of the Vita classic shade guide, and Chromoscop® universal shade guide.

Thus, it would be extremely beneficial to have pre-shaded YTZP blocks or blanks that sinter isotropically to full density and that yield the required variety of shades consistently and without compromise in strength, fracture toughness, and reliability or Weibull modulus.

SUMMARY

The present invention provides compositions and methods that can optionally address one or more of the abovementioned shortcomings associated with conventional technology, and provide shaded $ZrO_2$-based articles that sinter isotropically to full density, and possess at least adequate strength, fracture toughness, and a reliability or Weibull modulus >10 as required per the ASTM Standard for biomedical grade 3YTZP. The amount of coloring agent(s) contained in the $ZrO_2$-based articles can be relatively low, thereby minimizing any negative impact on the properties of the articles due to the presence of coloring agent(s) in the composition.

According to one aspect, the present invention provides a dental article; wherein the article may comprise a blank or block, a coping or framework for a dental restoration or implant, or an abutment; the article comprising: yttria stabilized tetragonal zirconia; and no more than about 0.15 wt. % of one or more coloring agents comprising one or more of: Pr, Tb, Cr, Nd, Co, oxides thereof, and combinations thereof, whereby the dental article is provided with a color corresponding to a natural tooth shade; wherein the dental article has a flexural strength of at least about 800 MPa when sintered to at least 98% of its theoretical density.

According to another aspect, the present invention provides a dental restoration comprising: (i) a core or framework, and (ii) an overlay. The core or framework comprising yttria stabilized tetragonal zirconia, and no more than about 0.15 wt. % of one or more coloring agents comprising one or more of: Pr, Tb, Cr, Nd, Co, oxides thereof, and combinations thereof, whereby the core or framework is provided with a tooth color corresponding to a natural tooth shade and the core or framework has a flexural strength of at least about 800 MPa when sintered to at least 98% of its theoretical density. The overlay may be porcelain and can be fused to the core or framework resulting in a final tooth-like appearance.

According to a further aspect, the present invention provides a method of forming a dental article, the method comprising: providing a first uncolored powder; combining at least one first coloring agent and a second powder thereby forming a first pigment powder; mixing the first uncolored powder and the first pigment powder, thereby forming a mixed powder; pressing the mixed powder to form a pressed body; and firing the pressed body; thereby producing a dental article comprising a color corresponding to a predetermined natural tooth shade, and a flexural strength of at least 800 MPa when sintered to at least 98% of its theoretical density.

According to an additional aspect, the method described above may further comprise: combining at least one second coloring agent and the second powder thereby forming a second pigment powder; mixing the first uncolored powder, the first pigment powder, and the second pigment powder, thereby forming the mixed powder.

According to yet an additional aspect, the method described above may further comprise: combining at least one third coloring agent and the second powder thereby forming a third pigment powder; mixing the first uncolored powder, the first pigment powder, and the second pigment powder, and the third pigment powder, thereby forming the mixed powder.

According to another aspect, the white powders and pigment powder combinations are made into liquid suspensions useful for injection-molding or rapid-prototyping feedstocks, that have a solids content of 2 to 90 wt. %. These suspensions or feedstocks are used to form dental articles via a number of techniques including gel casting, slip casting, freeze casting, electrophoretic deposition, injection molding, or rapid prototyping (also known as solid freeform fabrication). "Rapid prototyping" is the generic term for net-shape manufacturing of materials into complex shapes and includes, stereolithography, photo-stereolithography, digital light processing (DLP), selective area laser deposition, selective laser sintering (SLS), electrophoretic deposition (EPD), robocasting, fused deposition modeling (FDM), laminated object manufacturing (LOM), or 3-D printing, as described in greater detail in US Patent Application Publication No. 2005/0023710, which is incorporated hereby by reference.

The pigment powders can be colored to the three primary colors, i.e., yellow, pink and grey/blue, or colors that can be effectively used in lieu of primary colors in dental color space, i.e., brown or pinkish-mauve, in place of pink.

Additionally, we have discovered that the colorant Cr (pinkish), can be used in combination with other potent colorants, Pr (yellow), and Co (blueish grey), to achieve tooth colored zirconia. Remarkably, the total colorant amount required is on the order of only 0.035 wt. % (0.0063 mol. %).

In addition, according to the present invention, Cr has been found to be a potent coloring additive that, surprisingly, results in a pinkish-mauve color for sintered 3Y-TZP bodies with small Cr additions (on the order of 0.003 wt. % (0.005 wt. % $Cr_2O_3$)).

BRIEF DESCRIPTION OF THE DRAWING FIGURES

The following detailed description of preferred embodiments can be read in connection with the accompanying drawing in which:

FIG. 1 is a cross-sectional illustration of an example of a dental article formed according to the principles of certain embodiments of the present invention.

DETAILED DESCRIPTION

According to certain aspects of the present invention, there is provided a sintered ceramic body which is doped with or otherwise contains one or more coloring agents. The one or more coloring agents are selected so as to provide the sintered ceramic body with a desired color by incorporating a relatively small amount of the coloring agents into the composition of the sintered ceramic body. The relatively small amount of the addition of coloring agents advantageously minimizes any adverse impacts that the coloring agents might have on the properties of the sintered ceramic body.

According to the present invention, the ceramic body can take any suitable form, shape, or geometry. According to one embodiment, a sintered ceramic body is provided in the form of a dental article. Thus, the identity and amount of one or more coloring agents incorporated into the composition of the sintered ceramic body are chosen so as to provide the sintered ceramic body with a final color corresponding to a desired natural tooth color or shade. A number of different dental articles are contemplated. For example, dental articles formed according to the principles of the present invention can include: blocks or blanks suitable for subsequent machining; a prefabricated shape; supports or frameworks for a dental restorations; a coping; pontic; denture teeth; space maintainers; tooth replacement appliance; orthodontic retainer; denture; post jacket; facet; splint; cylinder; pin; connector; crowns; partial crowns; veneers; onlays; inlays; bridges; fixed partial dentures; Maryland Bridges; implant abutment. According to an illustrative example, a dental restoration formed according to the principles of the present invention is illustrated in FIG. 1. As illustrated therein, a dental restoration 10 can comprise a support or framework 20 in the form of a sintered ceramic body having a concentration containing one or more coloring agents according to the principles of the present invention, to which is bonded to an overlay material 30. The support or framework 20 can be formed of any suitable base ceramic material described herein, such as a stabilized yttria tetragonal zirconia polycrystalline material (YTZP), and one or more coloring agent having an identity and an amount as described further below. The overlay 30 can likewise be formed of any suitable overlay material, for example, an overlay of zirconia-porcelain material can be utilized.

According to one optional aspect of the present invention, the sintered ceramic body can comprise porous zirconia (e.g., YTZP) blocks or blanks, which are preshaded, optionally by any of the techniques described herein, and can optionally be processed by CAD/CAM techniques, then finally sintered to form colored dental frameworks of high strength. The term "blocks" and "blanks" are not intended to limit the geometry of the articles of the present invention. Any suitable CAD/CAM technique may be utilized in connection with the present invention. For example, such techniques are described in U.S. Pat. No. 7,011,522, which is incorporated herein by reference, in its entirety. The blocks or blanks can be in the as-pressed green state (with binder), or pre-sintered state (with binder removed). The blocks can have a pore volume of 40 to 80%, and can be sinterable to at least 99% of theoretical density yielding grain sizes of 0.2 to 1.5 μm, at sintering temperatures of 1150 to 1550° C., average flexural strengths in excess of 800 MPa, optionally in excess of 900 MPa, and optionally in excess of 1,000 MPa, when sintered to at least 98% of its theoretical density, are attainable. The blocks are machinable and are characterized by isotropic shrinkage during the sintering process enabling their processing by CAD/CAM techniques into dental restorations of high strength and excellent fit.

The ceramic body can comprise any suitable composition to which one or more coloring agents can be added. According to certain optional aspects, the base ceramic to which one or more coloring agents is added can comprise a stabilized ceramic. For example, the base ceramic can comprise a yttria stabilized tetragonal zirconia polycrystalline ceramic material (YTZP), calcia stabilized zirconia, magnesia stabilized zirconia, and/or ceria stabilized zirconia, all of which can be obtained commercially.

The base ceramic material can be doped or combined with one or more coloring agents. For example, the base ceramic composition can be doped with no more than 0.15 wt. %, optionally no more than 0.10 wt. %, optionally no more than 0.08 wt. %, or optionally no more than 0.07 wt. % of coloring agent(s) or additive(s). The above-mentioned amounts referred to the amounts of either the elemental, ionic, and/or oxide form of the agent(s) contained in the sintered ceramic body. The one or more coloring agents or additives can be selected from: Tb, V, Ce, Pr, Cr, Co, Nd, Ni, Cu, Ho, oxides thereof, and combinations thereof. Optionally, the one or more coloring agents can be selected from: Pr, Tb, Cr, Nd, Co, oxides thereof, and combinations thereof. The coloring agents can comprise: at least Pr and/or an oxide thereof; at least Pr, Cr, and/or oxides thereof; Pr, Cr, Co and/or oxides thereof; and at least Tb, Nd, and/or oxides thereof. Optionally, the coloring additives can consist essentially of: Pr and/or an oxide thereof; Pr, Cr, and/or oxides thereof; Pr, Cr, Co and/or oxides thereof; and Tb, Nd, and/or oxides thereof.

A sintered ceramic body including a small amount of one or more of the coloring agents, as described above can additionally possess good physical properties, such as a high flexural strength with a weibull modulus greater than 10. For example, a sintered ceramic body formed according to the present invention may have an average flexural strength in excess of 800 MPa, optionally in excess of 900 MPa, and optionally in excess of 1,000 MPa. The flexural strength is measured per a conventional three-point bend test.

The resulting colors of the as-sintered articles are suitable for dental restoration frameworks that can be overlaid with a suitable overlay material, such as a zirconia-porcelain system, to achieve tooth-colored shades for the finished restoration.

The present invention is also directed to methods or techniques for coloring sintered ceramic bodies. According to one illustrative technique, an uncolored base ceramic powder can be combined with one or more additional powders which contain one or more coloring agents or additives. These additional powders can be termed "pigments" or "pigment powders." Once these powders have been combined, they can then be processed according to conventional techniques to produce a finished sintered body possessing the desired coloration, and mechanical properties.

The uncolored base ceramic powder can have any suitable composition, such as including any of the compositions described above for base ceramic materials (e.g., YTZP). Similarly, the one or more coloring agents or additives can also comprise any one, or combination of, the coloring agents or additives described above. According to the principles of the present invention, the amount of the one or more coloring agents contained in the pigment powders, as well as the proportions of the uncolored base ceramic and pigment powders, are calculated so as to provide a finished sintered body having a desired total quantity of coloring agents contained therein. This calculation can be performed according to conventional techniques familiar to those skilled in the art, and which are further elucidated by reference to the following examples.

As pointed out in U.S. Pat. No. 6,030,209, the shading of dental porcelain to achieve tooth colors typically relies on blending of yellow, pink, grey/blue pigments (i.e., primary colors) with the "white" porcelain powder to achieve the desired tooth colors. Surprisingly, this model also seems appropriate for shading of zirconia, as demonstrated in the following examples. In embodiments of the invention herein, the inventors are able to provide "pigment" powders in order to shade zirconia powder to achieve ΔE of 2 or less, i.e., matching target color (shade) in a color space (L*a*b* color space) within 2 units or less, as described in U.S. Pat. No. 6,030,209.

Examples 1 to 8 below illustrate how coloring formulations can be developed via immersion of pre-sintered blanks in solutions comprising coloring additives. Example 4 also illustrates sintered bodies that have been provided with colors using a relatively small amounts of coloring agent. Examples 9 to 11 illustrate combining YTZP powder with one or more coloring additives by immersion of as-received powder in solutions comprising coloring additives in ionic or complex form. Examples 12 and 13 illustrate combining YTZP powder with one or more coloring additives by combining YTZP powder and one or more pigment powders that have been doped with at least one coloring additive.

In alternative embodiments of the present invention the doped powder is fabricated by introduction of coloring additives as individual oxides or other precursor forms before, during, or after one of the stages of the manufacturing of said powder such as hydrolysis, drying, calcination, milling, or spray drying processing steps. These precursor forms include but are not limited to individual or complex oxides, salts, inorganic or organic and organo-metallic compounds (and combinations thereof) added in the form of aqueous or non-aqueos solutions, emulsions, dispersions, gels and particulates. All concentrations that are referred to in the examples are by weight percentage.

The salts used in the examples are all commercially available and were obtained from Alfa Aesar, Ward Hill, Mass. The zirconia powders that were used in the examples were the commercially available 3Y-TZP grades, TZ-3YB-E, and TZ-3YB, from Tosoh USA, Inc., Grove City, Ohio. The TZ-3YB-E grade contains approximately 0.25 wt. % alumina, and the TZ-3YB grade is essentially alumina-free. For the examples in which it was used, the TZ-3YB grade is explicitly indicated. All other examples used the TZ-3YB-E grade. All firing cycles were done in an air atmosphere. The densities and flexural strengths reported for select sintered specimens were measured by the Archimedes method, and per ISO 6872, respectively. Color was evaluated as necessary, both visually, by a certified dental technician, and measured on a white background using a ColorTec-PSM™ spectrophotometer from ColorTec™, Clinton, N.J. The color parameters were read in reference to D65/10° illuminations standard. Fluorescence in the visible light range was evaluated using a model UVL-56 BLAK-RAY® Lamp, Longwave UV-365 nm, ultraviolet light box from UVP, Upland, Calif.

EXAMPLE 1

Salts of Pr, Ce, Tb, V, Fe, Er, Cr, Eu, Ho, Co, Nd, Ni, and Cu were dissolved in distilled water in the proportions shown in Table 1. Zirconia discs, 27 mm diameter×2.75 mm thick, were pressed (10 MPa, uniaxial) from TZ-3YB-E powder and subsequently fired by heating at 1° C./m to 700° C., holding for 2 h (debinderization), followed by heating, at 4° C./m to 1100° C., holding for 2 h (presintering), and then cooling at 4° C./m to ambient. The presintered density was approximately 3.15 g/cc. Presintered zirconia discs were immersed in the salt solutions for 10 minutes, removed and then fired by heating at 4° C./m to 150° C., holding for 2 h (drying), followed by heating at 4° C./m to 1500° C., holding for 2 h (sintering), and then cooling at 4° C./m to ambient. The same firing was also given to a "control", i.e., a presintered disc that had not been immersed in solution. The resulting colors are listed in Table 1, and include yellow, pinkish-mauve (where "mauve" is defined as a "moderate purple"), pink, grey, blue and green. The control fired to a translucent white color.

TABLE 1

| Element | Solution | Color |
|---|---|---|
| Pr | 0.5% Praseodymium (III) acetate hydrate | Yellow |
| Ce | 10% Ce(III) nitrate | Yellow |
| Tb | 0.05% terbium(III) chloride hexahydrate | Yellow-orange |
| V | 0.1% vanadium(IV) fluoride | Yellow |
| Fe | 1% Iron(II) chloride | Yellow |
| Er | 10% Erbium (III) chloride hexahydrate | Light Pink |
| Cr | 0.05% Cr(III) chloride hexahydrate | Mauve |
| Eu | 10% Europium(III) Chloride Hydrate | White |
| Ho | 10% Ho(III) chloride | Yellow/pink |
| Co | 0.1% Co(II) chloride | Grey |
| Ni | 0.5% Ni(II) chloride | Green |
| Cu | 0.5% Cu(II) acetate | Green |
| Nd | 5% Nd(III) chloride hydrate | Light blue |

EXAMPLE 2

Solutions of Tb(III) chloride hexahydrate and V(IV) fluoride, of different concentrations were prepared (Table 2). Pre-sintered zirconia discs were immersed in the solutions and fired as per Example 1. The results are shown in Table 2 and demonstrate that the intensity of the color achieved, yellow, can be controlled by the solution concentration. Specifically, one can increase the yellow intensity by increasing solution concentration.

TABLE 2

| Solution | Color |
|---|---|
| Tb(III) chloride hexahydrate, % | |
| 0.005 | Pale yellow |
| 0.01 | medium yellow |
| 0.05 | Yellow |
| V(IV) fluoride, % | |
| 0.005 | pale yellow |
| 0.01 | pale yellow |
| 0.10 | yellow |

EXAMPLE 3

Solutions of Praseodymium (III) acetate hydrate and Cr(III) chloride hexahydrate, of different concentrations were prepared (Table 3). Pre-sintered zirconia discs were immersed in the solutions and fired as per Example 1. Some discs were sintered in the as-pre-sintered state, and were the controls. Flexural strengths were measured for as-fired surfaces using the 3-point-bend test configuration. The results are shown in Table 3. Again, the results show that the intensity of the color achieved, can be controlled by the solution concentration. Additionally, coloring with 0.01% Pr-acetate and 0.01% Cr-chloride does not appear to adversely affect densification or flexural strength, i.e., the densities and flexural strengths of Pr- and Cr-colored specimens was statistically the same as for the control.

TABLE 3

| Solution | Color | Density (g/cc) | Flexural Strength (MPa) |
|---|---|---|---|
| % Pr(III) acetate hydrate | | | |
| 1 | orange | — | — |
| 0.25 | dark yellow | 6.00 | — |
| 0.10 | medium yellow | 6.05 | 1,106 ± 327 (n = 8) |
| 0.05 | yellow | 6.08 | — |
| 0.01 | pale yellow | — | — |
| % Cr(III) chloride hexahydrate | | | |
| 0.10 | dark pinkish-mauve | 6.07 | 1,099 ± 184 (n = 10) |
| 0.05 | medium pinkish-mauve | 6.03 | — |
| 0.01 | light pinkish-mauve | — | — |
| None (control) | white | 6.07 | 1,153 ± 261 (n = 8) |

EXAMPLE 4

Three solutions were prepared by dissolving Praseodymium(III) acetate hydrate, Chromium(III) chloride hexahydrate, and Co(II) chloride in distilled water in the proportions shown in Table 4. Pre-sintered zirconia discs were immersed in the solutions and fired as per Example 1. The discs were thinned to 0.5 mm and the surface color was evaluated. The results are shown in Table 4 along with the calculated concentrations of the coloring additive ions as calculated based on the solution concentration and the assumption that during immersion, the solution completely filled the pore volume of the pre-sintered bodies.

TABLE 4

| Shade | % Pr(III) acetate hydrate | % Cr(III) chloride hexahydrate | % Co(II) chloride | Density (g/cc) | CIE L, a, b | Total Concentration of Coloring Ions (calculated) wt. % | Flexural Strength (MPa) |
|---|---|---|---|---|---|---|---|
| 1 | 0.025 | 0.025 | 0 | 6.07 | 81.78, 1.12, 18.05 | 0.0026 | n/a |
| 2 | 0.008 | 0.002 | 0 | n/a | 87.4, −0.37, 12.36 | 0.0007 | n/a |
| 3 | 0.024 | 0.005 | 0.005 | 6.07 ± 0.01 | 86.55, 0.34, 9.59 | 0.0024 | 921 ± 203 (n = 12) |

Shades 1, 2 and 3 did not fluoresce under UV illumination. Shades 1, 2 are considered appropriate core shade for some of the Vita Classic A, C and D shades, respectively. These results show that YTZP can be shaded via combinations of Pr, Cr and Co, to achieve coloration that is appropriate for dental frameworks.

EXAMPLE 5

Pre-sintered 25×10×2.5 mm³ TZ-3YB bars were machined by hand into a "shade tab" geometry using a dental handpiece with a diamond bur. This entailed shaping one end of the bar into a veneer that was approximately 0.6 mm in thickness. The shaped bar was immersed for 10 minutes in the coloring solution corresponding to Shade 1 of Table 4, and fired as per Example 1. The as-sintered shade tabs were nearly fully dense (6.05 g/cc), translucent, with a thickness of approximately 0.5 mm for the veneer portion. The veneer portion was overlayed with the zirconia porcelain, OPC 3G, Pentron Ceramics Inc., Somerset, N.J., to achieve tooth colored shade of approximately A1 of the Vita Classic shade guide.

EXAMPLE 6

A colored shade tab prepared as per Example 5 was overlayed with porcelain as per Example 5, to achieve a tooth colored shade of approximately A2 of the Vita Classic guide.

EXAMPLE 7

A pre-sintered shade tab prepared as per Example 5 was immersed for 10 minutes in the coloring solution corresponding to Shade 3 of Table 4, and fired as per Example 1. The resulting fully sintered specimen was overlayed with porcelain as per Example 5, to achieve a tooth colored shade of approximately D3 of the Vita Classic shade guide.

EXAMPLE 8

A 0.25 wt. % solution of Praseodymium (III) acetate hydrate in distilled water was prepared. Pre-sintered zirconia discs, 27 mm dia.×2.75 mm thick, and pellets 16 mm diameter by 10 mm tall, were prepared as per Example 1. These were immersed in the solutions for a range of times from 10 minutes up to 144 h, and fired as per Example 1. The resulting surface coloration was an orangish-yellow, and was approximately same for all specimens. The specimens were cross-sectioned revealing that the coloring depth increased with immersion time. The cores of all the specimens were white in color.

TABLE 5

| immersion time | Approximate Depth of coloration (mm) |
|---|---|
| 10 min | 0.25 |
| 2 h | 0.5 |
| 72 h | 2.5 |
| 144 h | 3 |

EXAMPLE 9

A 0.25 wt. % solution of Praseodymium(III) acetate hydrate in distilled water was prepared. The solution was added to TZ-3YB-E powder in a one-to-one ratio, by weight. The powder+solution combination was stirred thoroughly and then dried by heating to 150° C. and holding for 4 h. The dried powder was screened through a 170 mesh (90 μm) nylon screen, and pressed into discs as per Example 1. The discs were debinderized by heating at 1° C./m to 700° C., and holding for 5 h, followed by heating at 4° C./m to 1500° C., and holding for 2 h, to sinter the bodies, and then cooling at 1° C./m to ambient. This resulted in a dark-yellow colored body that was colored through the thickness and had a density of 6.07 g/cc. This example demonstrates that colored TZP blocks can be manufactured by immersing the powder in the coloring salt solution prior to drying followed by compaction.

EXAMPLE 10

Solutions of Praseodymium(III) acetate hydrate and Chromium(III) chloride hexahydrate in distilled water were prepared according to Table 6.

TABLE 6

| Solution | Pr(III) acetate hydrate (wt. %) | Cr(III) chloride hexahydrate (wt. %) | Distilled Water |
|---|---|---|---|
| 1 | 0.5 | 0 | Balance |
| 2 | 0 | 0.05 | Balance |
| 3 | 0 | 0 | Balance |

A third "solution", 100% water, served as the control. The solutions were individually added to TZ-3YB-E powder in a 8-to-25 ratio, by weight, and the combinations were thoroughly mixed. The resulting blends were subsequently freeze-dried for approximately 12 hours and screened through a 250 mesh (55 micron) nylon screen to yield a free-flowing powder. Discs, 27 mm diameter by 1.2 mm thick, were pressed from these powders as per Example 1, and fired by heating at 1° C./m to 700° C., and holding for 2 h (debinderization step), followed by heating at 4° C./m to 1500° C., and holding for 2 h (sintering step), and then cooling at 4° C./m to ambient. The results are shown in Table 7.

TABLE 7

| | Nominal coloring dopant content (wt. %) | | | | | Bend |
| Solution | Pr ($Pr_6O_{11}$) | Cr ($Cr_2O_3$) | Visual | Color CIE L, a, b | Density (g/cc) | Strength (MPa) |
|---|---|---|---|---|---|---|
| 1 | 0.0709 (0.0856) | 0 | Yellow | 82.15, 2.93, 37.12 | 6.09 | 1152 ± 208 |
| 2 | 0 | 0.0031 (0.0046) | Mauve | 81.49, 1.67, 7.67 | 6.05 | 997 ± 119 |
| 3 | 0 | 0 | white | 88.76, −0.14, 3.69 | 6.07 | 1026 ± 178 |

These results show that doping of TZ-3YB-E with approximately 0.07 wt. % Praseodymium(III) yields a yellow sintered body with no compromise in density and strength. Also, they demonstrate that doping with approximately 0.003 wt. % of Cr(III) yields a sintered body that is pinkish-mauve in color with no compromise in density and strength. For all cases, coloration was uniform and was through the thickness of the sintered samples.

EXAMPLE 11

Three solutions of Praseodymium(III) acetate hydrate+Chromium(III) chloride hexahydrate in distilled water were prepared according to Table 8.

TABLE 8

| Solution | Pr(III) acetate hydrate (wt. %) | Cr(III) chloride hexahydrate (wt. %) | Distilled Water |
|---|---|---|---|
| 4 | 0.0625 | 0.025 | Balance |
| 5 | 0.1875 | 0.03125 | Balance |
| 6 | 0.125 | 0.0625 | Balance |

These solutions were used to process TZ-3YB-E powders into sintered dics as per Example 10. Color and fluorescence evaluation was done as per Example 4 on discs that had been thinned to 0.5 mm. Visual color evaluation entailed comparing the colored discs to a 3M™ ESPE™ LAVA™ Frame Shade Tabs set available from Issaquah Milling Center, Issaquah, Wash. The set consists of 0.5 mm thick sintered zirconia specimens that had been shaded with the 3M™ ESPE™ LAVA™ Frame Shade Dyeing Liquids, 3M Center, St. Paul, Minn., to the core shades: FS1, FS2, FS3, FS4, FS5, FS6 and FS7. The results are presented in Table 9.

TABLE 9

| | Nominal coloring dopant content (wt.%) | | Color | | |
|---|---|---|---|---|---|
| Solution | Pr ($Pr_6O_{11}$) | Cr ($Cr_2O_3$) | Visual (vs. LAVA ™ frame shades) | CIE L, a, b | Density (g/cc) |
| 4 | 0.0089 (0.0107) | 0.0016 (0.0023) | Close to FS2 | 83.99, −0.55, 15.81 | 6.06 |
| 5 | 0.0267 (0.0322) | 0.0019 (0.0028) | Close to FS3 | 85.19, −1.44, 21.32 | 6.06 |
| 6 | 0.0177 (0.0214) | 0.0047 (0.0069) | Matches FS7 | 81.6, −0.04, 18.85 | 6.12 |

Tooth colorations were achieved, and for all cases the coloration was uniform and was through the thickness of the sintered samples. Additionally, the tooth colored specimens did not fluoresce under UV illumination. These results demonstrate that the coloring dopants, Pr and Cr, can be used in combination to achieve shades appropriate for achieving finished restorations that are tooth-colored. It is noteworthy that the dopant levels required are of very low concentrations, e.g., Pr <approximately 0.030% and Cr <approximately 0.005%.

EXAMPLE 12

Solutions of 0.75 wt. % Praseodymium(III) acetate hydrate and 0.25 wt. % Cr(III) chloride hexahydrate, in distilled water were prepared. These solutions were individually mixed with TZ-3YB-E powder, dried and screened, as per Example 10. This yielded powders nominally doped with 0.1063% Pr and 0.0156% Cr, respectively. The doped powders were then combined with as-received TZ-3YB-E powder in the following properties: 8.3725% Pr-doped+10.2564% Cr-doped+81.3711% as-received TZ-3YB-E powder, and blended for 15 minutes using a paint shaker. (The proportions were calculated to give the same bulk nominal Pr and Cr concentration as Solution 4 of Table 9.) Several sintered discs were prepared from the powders as per Example 10, and their color was evaluated as per Example 11. Remarkably, visually, the color of the discs was uniform when viewed at 1×, 4× and 8× magnifications. One of the discs was thinned to 0.5 mm in thickness and CIE L*, a*, b* color coordinates of 84.21, −0.85, 18.25, respectively, were determined. Visually this specimen matched LAVA core shade FS2. Also, it did not fluoresce under UV illumination. Strength was measured to be 1,161±178 MPa (n=8).

EXAMPLE 13

The doped powders of Example 12 were combined with as-received TZ-3YB-E power in the following proportions: 16.651% Pr-doped+30.1782% Cr-doped+53.2208% as-received TZ-3YB-E powder, and blended for 15 minutes using a paint shaker. (These proportions were calculated to give the same bulk nominal Pr and Cr concentration as Solution 6 of Table 9.) Several sintered discs were prepared from the powders as per Example 10, and their color was evaluated as per Example 11. Like in Example 12, visually, the color of the discs was uniform. One of the discs was thinned to 0.5 mm in thickness and CIE L*, a*, b* color coordinates of 80.64, −0.41, 19.37, respectively, were determined. Visually this specimen matched LAVA core shade FS7 and did not fluoresce under UV illumination. Strength was measured to be 1,025±178 MPa (n=7).

EXAMPLE 14

Zirconia powder with a composition corresponding to Solution 6 of Table 9 is pressed into cylindrical blocks that are 2.0 cm dia.×4.0 cm long. This is done with a wet-bag cold isostatic press at pressure of 200 MPa using polyurethane tooling. The blocks are heated at 1° C./m to 700° C., and held for 10 h (debinderization), followed by heating at 4° C./m to 1000° C., and holding for 2 h (presintering), and then cooling at 4° C./m to ambient. The green density of the pre-sintered blocks is approximately 3.15 g/cc.

Using the laser scanner, D-250™ 3D Scanner, 3Shape A/S Copenhagen, Denmark, models of a single-unit and 3-unit-bridge preparations are scanned to create a 3D digital model which are saved as STL files. Using these files, the dental CAD software, DentalDesigner™, 3Shape A/S Copenhagen, Denmark is used to design the corresponding frameworks. The 3D models are saved as a STL files. These are transferred to a commercial CAM device with the ability to enlarge 3D digital model by the appropriate enlargement factor. Using an enlargement factor of approximately 1.243, which is inputted into the CAM software, the presintered blocks are machined into an oversized single-unit and 3-unit-bridge frameworks. The as-machined frameworks are sintered as per Example 10. The resultant sintered frameworks are of high density (approximately 6.05 g/cc), translucent, and uniformly colored with a shade closely matching LAVA FS7. The fit of the as-sintered frameworks onto the starting models is determined to be acceptable. This is indicative of isotropic shrinkage during the sintering step. The as-sintered frameworks are overlayed with Noritake Cerabien CZR Porcelain, Noritake Company, Inc., Fairlawn, N.J., to achieve a final VITA classic shade D2. The fit of the finished restorations to the starting models are determined to be acceptable. Shades and fit are evaluated by a certified dental technician.

EXAMPLE 15

Zirconia powder prepared as per Example 12 is processed into cylindrical CAD/CAM blocks as per Example 14. The blocks are then processed into sintered single-unit and 3-unit-bridge frameworks as per Example 14. The resultant sintered frameworks are of high density (approximately 6.05 g/cc), translucent, and uniformly colored with a shade closely matching LAVA FS2. The fit of the as-sintered frameworks onto the starting models is determined to be acceptable. The as-sintered frameworks are overlayed with Noritake Cerabien CZR Porcelain, Noritake Company, Inc., Fairlawn, N.J., to achieve a final VITA classic shade A2. The fit of the finished restorations to the starting models are determined to be acceptable. Shades and fit were evaluated by a certified dental technician.

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. For example, any numerical value may inherently contains certain errors resulting from the standard deviation found in their respective measurement techniques or in rounding off of measured values. None of the elements recited in the appended claims should be interpreted as invoking 35 U.S.C. §112, ¶6, unless the term "means" is explicitly used.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

We claim:

1. A method of forming a dental ceramic restorative article, the method comprising:
providing a first uncolored powder, wherein the first uncolored powder comprises zirconia;
combining at least one first coloring agent and a second powder thereby forming a first pigment powder, wherein the first coloring agent is a salt, oxide, inorganic compound, organic compound, organo-metallic compound or a combination thereof and wherein the second powder comprises zirconia;
mixing the first uncolored powder and the first pigment powder, thereby forming a mixed powder;
wherein an amount of the first coloring agent contained in the first pigment powder is selected, a proportion of first pigment powder and first uncolored powder in the mixed powder is selected, so as to provide the resulting dental restorative article with a tooth color having CIE L*, a*, b* color coordinates matching a shade standard within CIE L*, a*, b* color space region associated with tooth colors;
shaping the mixed powder to form a shaped body; and
firing the shaped body to at least 98% of its theoretical density;
thereby producing a dental restorative article comprising a color corresponding to a predetermined natural tooth shade and a flexural strength of at least 800 MPa.

2. The method of claim 1, wherein the first uncolored powder comprises yttria stabilized tetragonal zirconia polycrystalline ceramic.

3. The method of claim 1, wherein the second powder comprises yttria stabilized tetragonal zirconia polycrystalline ceramic.

4. The method of claim 1, further comprising: combining at least one second coloring agent, wherein the second coloring agent is a salt, oxide, inorganic compound, organic compound, organo-metallic compound or a combination thereof and the second powder thereby forming a second pigment powder; mixing the first uncolored powder, the first pigment powder, and the second pigment powder, thereby forming the mixed powder, wherein an amount of the second coloring agent contained in the second pigment powder is selected, a proportion of second pigment powder, first pigment powder, and first uncolored powder in the mixed powder is selected, so as to provide the resulting dental restorative article with a tooth color having CIE L*, a*, b* color coordinates matching a shade standard within CIE L*, a*, b* color space region associated with tooth colors.

5. The method of claim 4, further comprising: combining at least one third coloring agent, wherein the third coloring agent is a salt, oxide, inorganic compound, organic compound, organo-metallic compound or a combination thereof and the second powder thereby forming a third pigment powder; mixing the first uncolored powder, the first pigment powder, the second pigment powder, and the third pigment powder, thereby forming the mixed powder, wherein an amount of the third coloring agent contained in the second pigment powder is selected, a proportion of third pigment powder, second pigment powder, first pigment powder, and first uncolored powder in the mixed powder is selected, so as to provide the resulting dental restorative article with a tooth color having CIE L*, a*, b* color coordinates matching a shade standard within CIE L*, a*, b* color space region associated with tooth colors.

6. The method of claim 5, wherein the at least one first coloring agent and the at least one second coloring agent, and at least one third coloring agent comprise at least one of: Pr, Tb, Cr, Nd, Co, Ni, salts thereof, oxides thereof, and combinations thereof.

7. The method of claim 4, wherein the at least one first coloring agent and the at least one second coloring agent comprise at least one of: Pr, Tb, Cr, Nd, Co, Ni, salts thereof, oxides thereof, and combinations thereof.

8. The method of claim 4, further comprising selecting an amount of first coloring agent contained in the first pigment powder, selecting an amount of second coloring agent in the second pigment powder, and selecting a proportion of first pigment powder, second pigment powder, and first uncolored powder in the mixed powder, so as to provide the resulting dental restorative article with no more than a total of about 0.15 wt. % total coloring agent.

9. The method of claim 4, further comprising selecting an amount of first coloring agent contained in the first pigment powder, selecting an amount of second coloring agent in the second pigment powder, and selecting a proportion of first pigment powder, second pigment powder, and first uncolored powder in the mixed powder, so as to provide the resulting dental restorative article with no more than a total of about 0.10 wt. % total coloring agent.

10. The method of claim 4, further comprising selecting an amount of first coloring agent contained in the first pigment powder, selecting an amount of second coloring agent in the second pigment powder, and selecting a proportion of first pigment powder, second pigment powder, and first uncolored powder in the mixed powder, so as to provide the resulting dental restorative article with no more than a total of about 0.08 wt. % total coloring agent.

11. The method of claim 4, further comprising selecting an amount of first coloring agent contained in the first pigment powder, selecting an amount of second coloring agent in the second pigment powder, and selecting a proportion of first pigment powder, second pigment powder, and first uncolored powder in the mixed powder, so as to provide the resulting dental restorative article with no more than a total of about 0.07 wt. % total coloring agent.

12. The method of claim 1, wherein the at least one first coloring agent comprises at least one of: Pr, Tb, Cr, Nd, Co, Ni, salts thereof, oxides thereof, and combinations thereof.

13. The method of claim 1, further comprising selecting an amount of first coloring agent contained in the first pigment powder, and selecting a proportion of first pigment powder and first uncolored powder in the mixed powder, so as to provide the resulting dental restorative article with no more than a total of about 0.15 wt. % total coloring agent.

14. The method of claim 1, further comprising selecting an amount of first coloring agent contained in the first pigment powder, and selecting a proportion of first pigment powder and first uncolored powder in the mixed powder, so as to provide the resulting dental restorative article with no more than a total of about 0.10 wt. % total coloring agent.

15. The method of claim 1, further comprising selecting an amount of first coloring agent contained in the first pigment powder, and selecting a proportion of first pigment powder and first uncolored powder in the mixed powder, so as to provide the resulting dental restorative article with no more than a total of about 0.08 wt. % total coloring agent.

16. The method of claim 1, further comprising selecting an amount of first coloring agent contained in the first pigment powder, and selecting a proportion of first pigment powder and first uncolored powder in the mixed powder, so as to provide the resulting dental restorative article with no more than a total of about 0.07 wt. % total coloring agent.

17. The method of claim 1, wherein the dental restorative article comprises a block or blank, a support or framework for a dental restoration, a crown, a partial crown, a veneer, an onlay, an inlay, a bridge, fixed partial dentures, a Maryland bridge, an implant abutment, or whole implant.

18. The method of claim 1, wherein the step of firing the pressed body comprises drying and binder removal steps, followed by a sintering step.

19. The method of claim 18, wherein the sintering step comprises at least one of: partial sintering, bisque sintering, soft-sintering, sintering to full density, densification, annealing and tempering.

20. The method of claim 1, where firing step comprises one or more heating segments performed in sequence one after the other, or interrupted in between.

21. The method of claim 1, wherein the shaping step comprises one or more of: compaction, extrusion, pressing, uniaxial pressing, cold isostatic pressing, casting, centrifugal casting, gravity casting, pressure casting, gel casting, slip casting, or slurry casting, freeze casting, injection molding or electrophoretic deposition.

22. The method of claim 1, wherein the mixing step comprises one or more of: dry-mixing, mixing in liquid medium, ball milling, spray drying, fluidized bed processing, freeze granulation, freeze drying, high shear mixing and granulation.

23. The method of claim 1, wherein the shaping step comprises rapid-prototyping by stereolithography, photo-stereolithography, digital light processing (DLP), selective area laser deposition, selective laser sintering (SLS), electrophoretic deposition(EPD), robocasting, fused deposition modeling (FDM), laminated object manufacturing (LOM), or 3D printing.

24. The method of claim 1, further comprising processing the shaped body into a dental restoration, dental prosthesis or part thereof by machining using CAD/CAM, CAM, CNC or other milling machines.

25. The method of claim 1, wherein the dental restorative article further comprises less than about 0.1 wt. % aluminum oxide.

26. A method of forming a dental restorative article, the method comprising:
providing a first uncolored powder, wherein the first uncolored powder comprises zirconia;
combining at least one first coloring agent and a second powder thereby forming a first pigment powder, wherein the first coloring agent is a salt, oxide, inorganic compound, organic compound, organo-metallic compound or a combination thereof and wherein the second powder comprises zirconia;
combining a second coloring agent and a third powder thereby forming a second pigment powder, wherein the second coloring agent is a salt, oxide, inorganic compound, organic compound, organo-metallic compound or a combination thereof;
mixing the first uncolored powder, the first pigment powder, and the second pigment powder thereby forming a mixed powder, wherein an amount of the second coloring agent contained in the second pigment powder is selected, a proportion of second pigment powder, first pigment powder, and first uncolored powder in the mixed powder is selected, so as to provide the resulting dental restorative article with a tooth color having CIE L*, a*, b* color coordinates matching a shade standard within CIE L*, a*, b* color space region associated with tooth colors;
shaping the mixed powder to form a shaped body; and
firing the shaped body to at least 98% of its theoretical density;
thereby producing a dental restorative article comprising a color corresponding to a predetermined natural tooth shade, and a flexural strength of at least 800 MPa.

27. The method of claim 26, wherein the flexural strength is at least 1200 MPa.

28. The method of claim 26, wherein the first, second and third powders are the same powder.

29. The method of claim 28, wherein the same powder comprises yittria stabilized tetragonal zirconia polycrystalline ceramic powder.

30. The method of claim 29, wherein the yittria stabilized tetragonal zirconia polycrystalline ceramic powder comprises less than 0.1 wt. % aluminum oxide.

31. The method of claim 29, wherein the yittria stabilized tetragonal zirconia polycrystalline ceramic powder comprises a binderized, ready-to-press powder.

* * * * *